United States Patent [19]

Horn et al.

[11] Patent Number: 5,342,582
[45] Date of Patent: Aug. 30, 1994

[54] APPARATUS FOR REPROCESSING SPECIAL WASTE

[75] Inventors: Klaus Horn, Hofheim am Taunus; Juergen Lingnau, Mainz-Laubenheim; Horst Weiler, Kiedrich, all of Fed. Rep. of Germany

[73] Assignee: Morton International, Inc., Chicago, Ill.

[21] Appl. No.: 42,582

[22] Filed: Apr. 5, 1993

[30] Foreign Application Priority Data

Apr. 10, 1992 [DE] Fed. Rep. of Germany ....... 4212118

[51] Int. Cl.$^5$ .................. A61L 2/00; B02B 7/02; B02C 19/00; C08F 2/48
[52] U.S. Cl. ..................... 422/105; 241/100; 241/235; 241/DIG. 38; 250/504 R; 422/24; 422/40; 422/186.05; 422/186.3; 422/131
[58] Field of Search ............ 422/131, 22, 24, 40, 422/105, 107, 117, 186.05, 186.3; 241/100, 235, 236, 606, DIG. 38; 250/492.1, 504 R

[56] References Cited

U.S. PATENT DOCUMENTS

| | | | |
|---|---|---|---|
| 2,683,689 | 7/1954 | Nichols | 422/24 |
| 3,981,687 | 9/1976 | Vig | 422/24 |
| 4,306,955 | 12/1981 | Neél et al. | 204/159.22 |
| 4,762,862 | 8/1988 | Yada et al. | 522/3 |
| 4,869,433 | 9/1989 | Leuellin | 422/24 |
| 4,889,290 | 12/1989 | Koffsky et al. | 241/606 |
| 4,902,482 | 2/1990 | Faust | 422/24 |
| 4,961,541 | 10/1990 | Hashimoto | 241/606 |
| 4,981,650 | 1/1991 | Brown et al. | 422/24 |
| 5,209,411 | 5/1993 | Dineley et al. | 241/606 |

FOREIGN PATENT DOCUMENTS

| | | |
|---|---|---|
| 0417714 | 3/1991 | European Pat. Off. . |
| 9205022 | 7/1992 | Fed. Rep. of Germany . |
| 2596765 | 10/1987 | France . |

Primary Examiner—Robert J. Warden
Assistant Examiner—L. M. Crawford
Attorney, Agent, or Firm—Gerald K. White

[57] ABSTRACT

An apparatus for reprocessing special waste of photocrosslinkable scrap material is composed of a housing equipped with a feed hopper, one or more UV emitters arranged in the housing to irradiate the scrap material, and a chopper arranged in the housing to comminute the scrap material by chopping. The apparatus is usefully employed in a method for reprocessing photocrosslinkable scrap material.

13 Claims, 3 Drawing Sheets

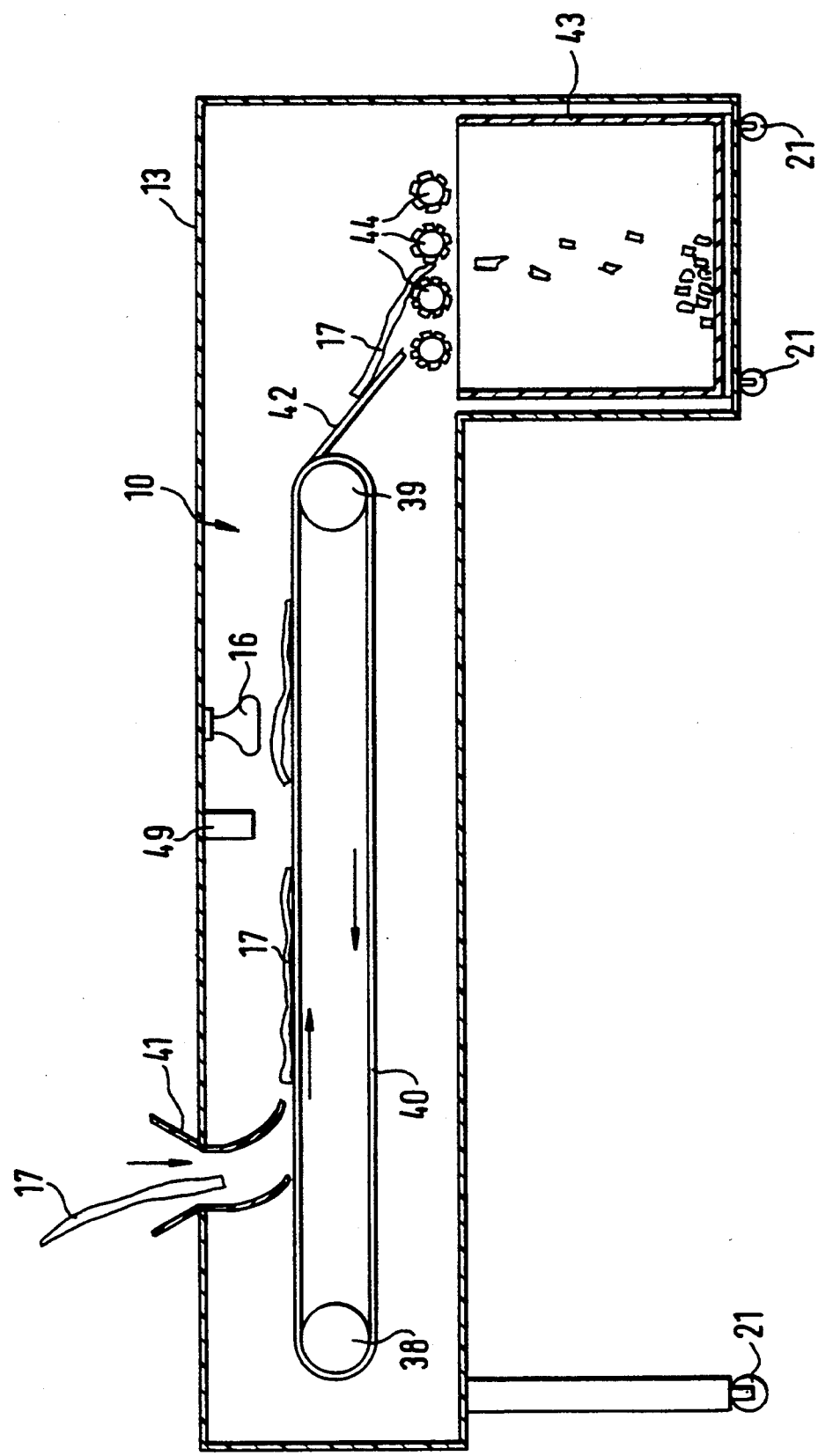

APPARATUS FOR REPROCESSING SPECIAL WASTE

BACKGROUND OF THE INVENTION

1. Field of the Invention

The invention relates to an apparatus useful for reprocessing special waste containing photocrosslinkable scrap to give domestic waste.

2. Description of Related Art

Photocrosslinkable waste materials arise from many process areas. For example, photocrosslinkable materials, such as dry resists, are used in the production of printed circuit boards. These dry resists are light sensitive materials containing a film which is applied by lamination using pressure and heat to the surface of a support material and is converted by exposure and development to a masking layer. Waste material from such a process since it is photocrosslinkable can generally not be disposed of as normal waste, similar to domestic waste, but must be treated as a special waste. This special waste must correspondingly be disposed of in a complex and thus higher cost manner.

Furthermore, in the lamination of printed circuit boards, dry resist strips are generally produced as scrap material, the surfaces of which are photocrosslinkable and thus must be disposed of as special waste.

Also, photopolymer layers which change their adhesive properties as a result of irradiation are, for example, used in the production of color proof films. These are usually light-sensitive layers which are enclosed in a sandwich-like manner between two different support materials, generally films, of which one is transparent to the irradiation. If the two support materials separate following the irradiation, the unexposed parts of the photopolymer layer remain adhered to the one support material, while the exposed parts of the photopolymer layer, on the other hand, adhere to the other support material.

The production of such color proof films gives unexposed waste strips, i.e., photocrosslinkable waste strips, which must be disposed of as special waste.

Such special waste is likewise produced in the processing of solder resist in the form of a solder mask. Solder resist is fundamentally a photocrosslinkable resist, the processing parameters and irradiation results of which differ somewhat from those for dry resist. If support materials or printing films are treated with photocrosslinkable solder resist, the scrap must be disposed of as special waste.

The thermally crosslinkable components produced in systems such as those described above must be converted into unreactive material by the action of heat before being disposed of as normal waste. Scrap from screen printing films can also be disposed of as normal waste by photocrosslinking the scrap.

SUMMARY OF THE INVENTION

An object of the invention is to provide an apparatus which reprocesses photocrosslinkable and thermally crosslinkable scrap composed of, for example, dry resist, solder resist, color proof films, screen printing films, and the like, which form special waste because of their reactive constituents, in such a manner that direct disposal as normal or domestic waste is possible.

In accordance with this object, there has been provided, an apparatus useful for reprocessing special wastes of photopolymerizable scrap material to produce domestic waste, comprising a housing equipped with a feed hopper, at least one UV emitter arranged in the housing to irradiate and heat the scrap material, and a chopper arranged in the housing to comminute the scrap material by chopping.

Further objects, features, and advantages of the present invention will become apparent from the detailed description of preferred embodiments which follows.

BRIEF DESCRIPTION OF THE DRAWINGS

The invention is described below in more detail with reference to illustrative embodiments represented as drawings, in which:

FIG. 3 shows, in a diagrammatic sectional view, a third embodiment of the apparatus according to the invention.

DETAILED DESCRIPTION OF THE PREFERRED EMBODIMENTS

The apparatus according to the invention contains a housing equipped with a feed hopper, a UV emitter, and a chopper. Any apparatus having these components which is useful in reprocessing photopolymerizable scrap is within the scope of the present invention. In an example of an arrangement of the invention, the housing sits as a removable or openable component on a prismatic container open at the top which is provided with a door and contains a removable waste sack for the comminuted scrap material.

The various elements of the apparatus can be arranged so that the chopper is provided downstream or upstream of the UV emitter or emitters. In an embodiment of the invention, the apparatus contains a horizontal, endless transport belt circulating round two deflection rollers arranged in the housing, wherein a feed hopper extends into the interior of the housing and ends above the transport belt, and wherein at least one UV emitter is mounted above the transport belt and at a distance from the feed hopper and a chopper is provided displaced to the side of and below the transport belt.

As a result of the irradiation and heating of the photocrosslinkable or thermally crosslinkable scrap with the aid of the UV emitter or emitters, and by the comminution of the scrap, where the scrap can either be first irradiated and then comminuted or first comminuted and then irradiated, the scrap is completely polymerized so that no photochemical or thermal processes can proceed any longer under the action of sunlight and so that leaching by rain or percolating water cannot occur. Scrap treated in this manner can therefore be disposed of as domestic waste without reservation.

The advantage is thus achieved by the apparatus and process according to the invention that the costs for disposal of special waste can be reduced by the disposal of the scrap as domestic waste and, furthermore, as a result of the comminution of the scrap into small part-strips, such as of about 10 to 15 mm in length, a significant reduction in volume is achieved in comparison to uncomminuted scrap material.

The apparatus can be used to reprocess any type of waste which includes photocrosslinkable or thermally crosslinkable components. The methods of reprocessing is described below with reference to the apparatus shown in the figures.

Figure 1:
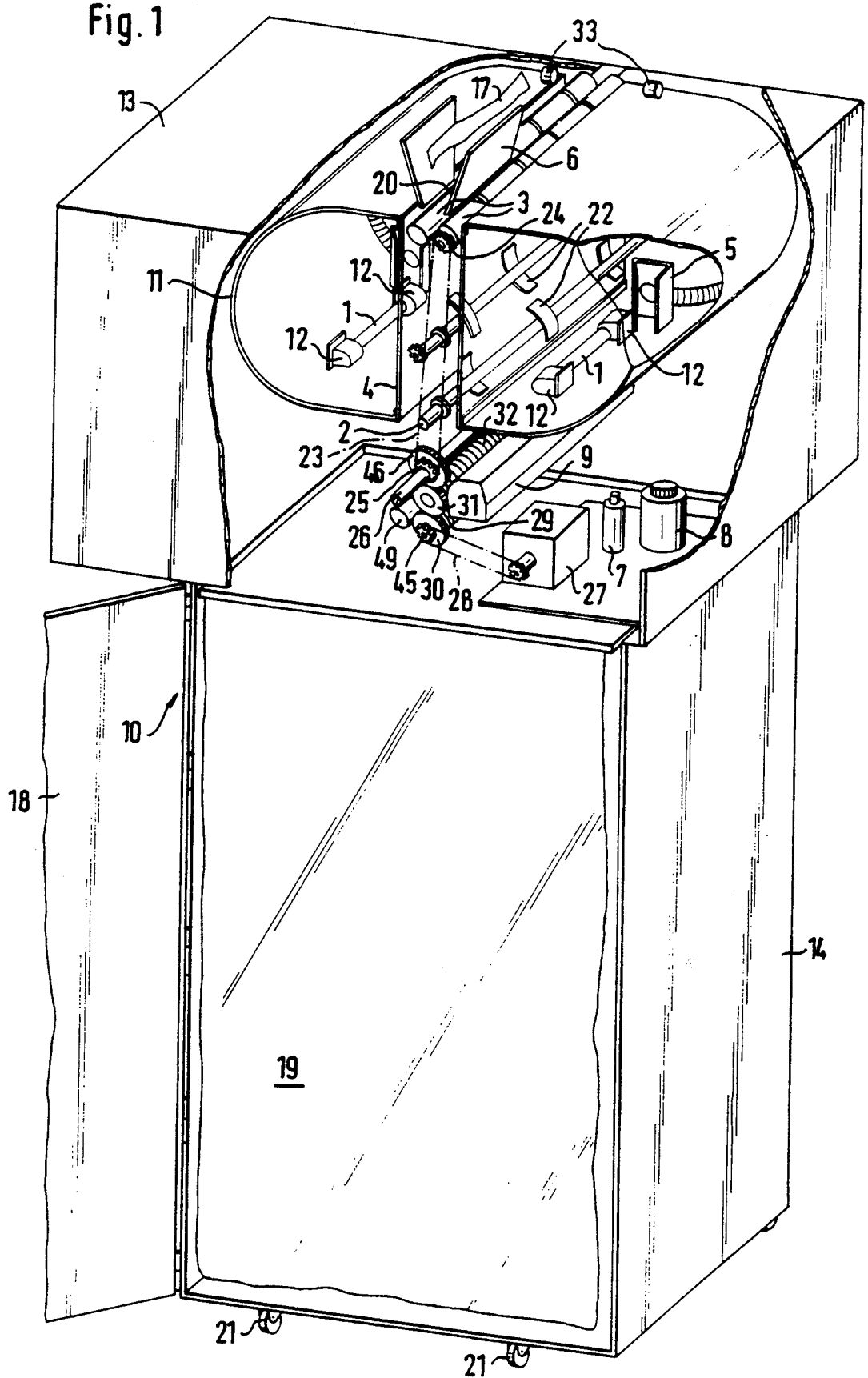
FIG. 1 shows, in a partially cut-away perspective representation, a first embodiment of the apparatus according to the invention.

In FIG. 1, a first embodiment of an apparatus 10 according to the invention is depicted. The apparatus 10 includes a housing 13, which sits on a prismatic container 14. The housing 13 is either designed to be removable from the container 14 or can be opened up from this by means of an undepicted hinge which, for example, extends over one of the narrow sides of the container 14. In the container 14, which is closed by an openable door 18, is located a removable waste sack 19 which receives comminuted scrap material leaving a chopper 9 in the housing 13. In the housing 13, UV emitters 1, which irradiate the scrap material, are located on both sides of the transport path of the scrap material 17. In FIG. 1, the UV emitters 1 are mounted horizontally in holders 12. Although this is not depicted in FIG. 1, the UV emitters can also be arranged vertically in such holders.

The chopper 9 is arranged downstream in the transport direction of the scrap material 17 of the UV emitters 1 which are surrounded by curved UV reflectors 11. The chopper 9 is a device resembling a shredder, as is used, for example, in shredding devices known per se. A feed hopper 6 is located on the top of the housing 13, which feed hopper merges into a feed slot 20 of an insert 4. Feed rolls 3 for the scrap material 17 are arranged in the feed slot 20, which scrap material 17 is diagrammatically indicated in FIG. 1 as waste strips. In the feed slot 20 moreover, is located a photocell 33 which controls the switching on and off of a motor 27 which sets both the chopper 9 and the feed rolls 3 in motion as will be described in more detail below. The photocell 33 controls the switching on and off of the motor 27 in accordance with the intake and throughflow of the scrap material 17, which, with the aid of flights (guides) 22 which are mounted on transport shafts 2, is transported into the chopper 9 situated below. The feed rolls 3, the transport shafts 2 and the chopper 9 are arranged in the insert 4 which is composed of UV-transparent material, such as UV transparent glass or UV transparent plastic. In FIG. 1, the UV emitters 1 are orientated horizontally, but it is equally possible that the UV emitters are arranged vertically and the associated UV reflectors 11 are, accordingly, also arranged vertically. Each of the UV emitters 1 is hit by cooling air from an air feed 5 in order to cool down the ambient air around the emitter, which air is greatly heated during operation of the emitter. The heated ambient air causes, for example, the thermal crosslinking of scrap which, in addition to a photocrosslinkable component, also contains a thermally crosslinkable component.

As already mentioned, the feed rolls 3 and the chopper 9 are driven by the motor 27. For this, the motor 27, via a sprocket chain 28, sets a first chopping shaft 29 of the chopper 9 in motion, the sprocket chain 28 being passed over a sprocket wheel 45 which is mounted as the end sprocket wheel on the first chopping shaft 29 of the chopper 9. Furthermore, the sprocket chain 28 runs over an end sprocket wheel which is not depicted in more detail and which is attached to the drive shaft of the motor 27. On the first chopping shaft 29 is additionally mounted a sprocket wheel 30 which is immediately adjacent to the sprocket wheel 45. The sprocket wheel 30 meshes with a sprocket wheel 31 on a second chopping shaft 32 of the chopper 9. This sprocket wheel 31 in turn engages with a further sprocket wheel 46 on the shaft 26 of the chopper 9. The sprocket wheel 46 is adjacent to the sprocket wheel 25. A continuous-loop sprocket chain 23 is passed over the sprocket wheel 25 and a sprocket wheel 24 on the axle of the one feed roll 3. The motor 27, via the sprocket chain 28, the sprocket wheels 30, 31 and 46 and the sprocket chain 23, thus simultaneously drives the chopper 9 and the feed rolls 3.

For the switching-on process of the UV emitters 1, a choke coil 8 and a starter 7 are provided to restrict the current uptake. The UV emitters 1 can be switched on by an undepicted switch which is actuated upon mounting the housing 13 on the container 14. As soon as the housing 13 is lifted or swung off from the container 14, the current supply to the UV emitters is interrupted by the switch. The photocell 33, as mentioned above, controls the start and stop of the feed rolls and the chopper. After the scrap material 17 has passed through the beam of the photocell 33, and after a certain delay, not only the feed rolls and the chopper but also the UV emitters are automatically shut off.

During comminution of the scrap in the chopper 9, high electrostatic charges occur on the resulting fine particles, which leads to these fine particles adhering to various points of the apparatus in the interior of the housing 13. In order to prevent this, an ionizing device 49, for example an ionizing rod to which a high frequency voltage is applied, is mounted in the housing interior in the vicinity of the chopper 9, generally below the chopping shafts. The ambient air of the chopper is ionized by this ionizing device and, as a result, the electrostatic charges are conducted away from the fine particles so that the fine particles no longer adhere to the various points in the apparatus interior.

Figure 2:
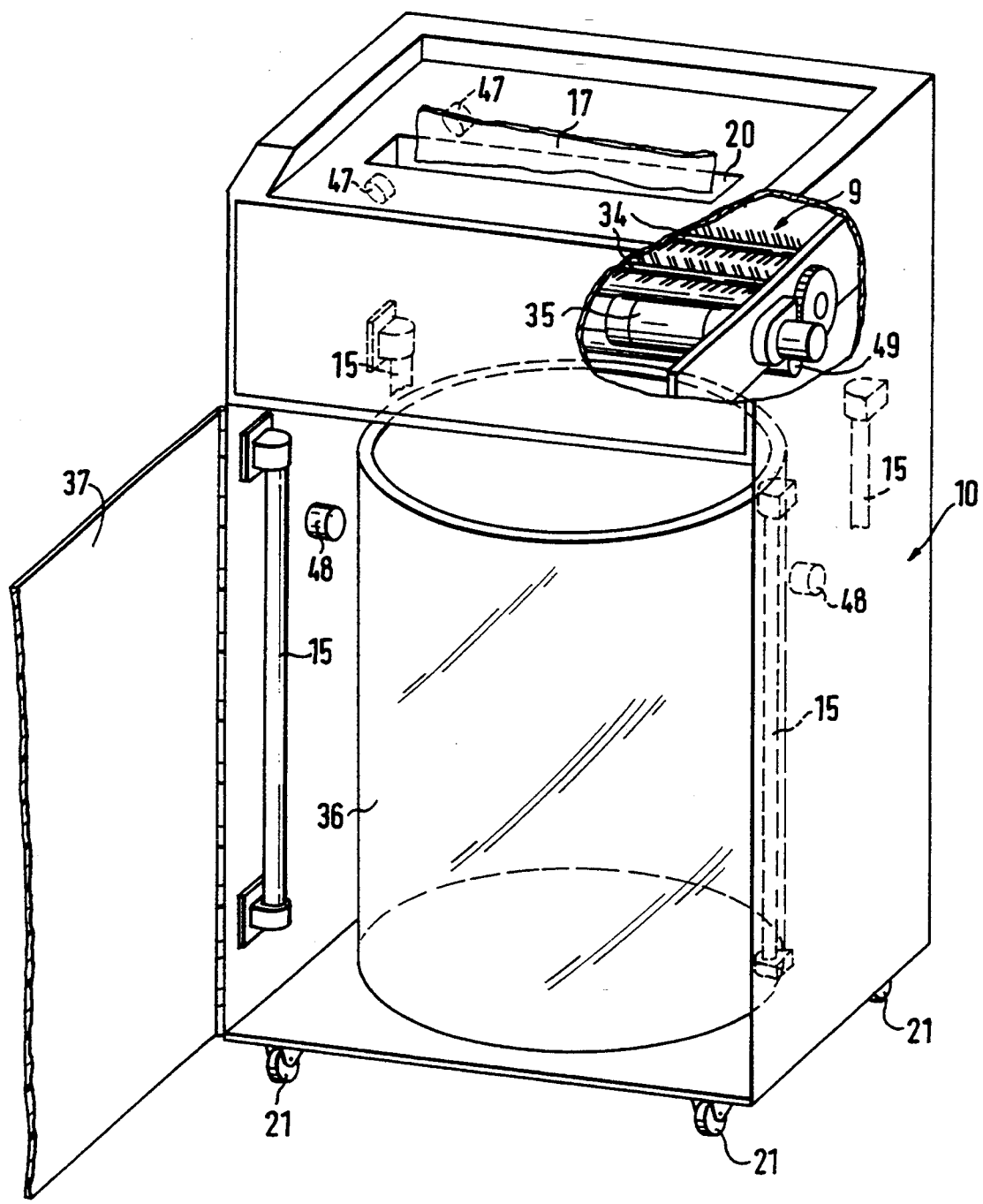
FIG. 2 shows, in a partially cut-away perspective representation, a second embodiment of the apparatus according to the invention.

FIG. 2 shows a further embodiment of the apparatus 10 according to the invention. In this embodiment, the chopper 9 is upstream of the UV emitters and is located below the feed slot 20. The chopper 9 carries out a chopping action, the particle size dimensions of the resulting chopped scrap material being in the range of about 2 mm · (10–15) mm. The chopper is equipped with two chopping shafts 34, one of which is directly driven by a motor 35. Below the chopper 9 are located an ionization device 49 and a cylindrical insert 36, into which the particles of the chopped scrap material 17 fall. The insert 36 is composed of a cylindrical UV-transparent glass or plastic container which is removable after opening a flap door 37. A plurality of rod-shaped UV emitters 15 are arranged vertically around the outside of the casing of the insert 36 at equal intervals, which UV emitters are switched on when the flap door 37 is closed and are switched off when this flap door is opened. The UV emitters 15 can also be mounted horizontally on the inner side of the housing of the apparatus 10. It is equally possible to use only a single UV irradiation source of appropriate strength so long as its radiation strength is sufficient to completely polymerize the particles of the scrap material. Instead of the rod-shaped UV emitters, incandescent bulb-like UV radiation sources can also be used.

A photocell 47 is also provided in this second embodiment of the apparatus 10, in a similar manner to the first embodiment of the apparatus as shown in FIG. 1. The photocell is in the feed region, that is below the feed slot 20, and controls the start and stop of the chopper 9 and the switching on and switching off of the UV emitters 15 with a preset delay after the scrap material 17 has passed through the feed slot 20. After the scrap material has passed through the feed slot 20, the apparatus 10 is automatically switched off after this preset delay. In addition, in this embodiment, a level indicator 48 is provided which indicates the level of material in the cylindrical insert 36. As soon as the insert 36 is full, the chopper 9 and the UV emitters 15 are likewise automatically switched off. An undepicted safety switch likewise switches off the apparatus 10 upon opening of the flap door 37 when the insert 36 is to be removed for emptying.

In FIG. 3, a third embodiment of the apparatus 10 is illustrated diagrammatically, in which an endless conveyor belt 40, horizontally running over two deflection rollers 38, 39, is arranged in the housing 13. The scrap material 17 to be disposed of is fed via a feed hopper 41 on the top of the housing 13 of the apparatus 10. The feed hopper 41 extends into the interior of the housing 13 and ends just above the conveyor belt 40. The feed hopper 41 is curved in the housing interior in the direction of motion of the top strand of the conveyor belt 40. The scrap material 17 is introduced into the feed hopper 41 so that the photo-crosslinkable layer of the scrap material faces upwards when lying on the top strand of the conveyor belt 40. An ionization device 49 and at least one UV emitter 16 are arranged above the conveyor belt 40 at a distance from the feed hopper 41. A guide element 42 lies tangentially against the conveyor belt 40 in the region of the one end roller 39 and deflects the scrap material 17 lying on the conveyor belt 40 into a chopper 44 which is laterally displaced to the conveyor belt and arranged below this. The chopper 44 substantially corresponds to the chopper 9 as given in FIGS. 1 and 2, so details of this chopper will not be described. The scrap material chopped into particles in the chopper 44 falls into a scrap container 43 which is arranged below the chopper. The ionization device 49, instead of being mounted upstream of the UV emitter 16, can equally be mounted below the chopper 44.

This embodiment of the apparatus 10 generally makes do with a single UV emitter 16, thereby producing less heat, which in any case must be removed. With this apparatus, it is, inter alia, also expedient to design the conveyor belt 40 to be sufficiently long so as to arrange the chopper 44 and the scrap container 43 outside the area in which the scrap material is produced. This ensures that particles or flakes of chopped photocrosslinkable scrap material are substantially isolated from the processing area for the photocrosslinkable material.

Each of the embodiments of the apparatus 10 is equipped with castors 21 and is thus mobile.

What is claimed is:

1. An apparatus for reprocessing photopolymerizable scrap material to produce domestic waste, comprising:
   a housing equipped with means for receiving strips of photopolymerizable scrap material;
   at least one UV emitter means arranged in the housing to irradiate said photopolymerizable scrap material and effect complete polymerization of said material so that it is insoluble and inert and suitable for disposal as normal waste;
   a chopper arranged in the housing to comminute said photopolymerizable. scrap material into fine particles; and
   an ionizing means mounted in the housing interior in the vicinity of the chopper and being connected to a high frequency voltage source for ionizing the air in the housing to cause electrostatic charges to be conducted away from the comminuted particles so as to prevent said particles from adhering to the housing interior.

2. An apparatus as claimed in claim 1, further comprising a container having a top opening and a door, and a removable waste sack, wherein the housing removably sits on said container and wherein the waste sack is removably disposed in said container to receive the comminuted scrap material.

3. An apparatus as claimed in claim 2, further comprising a switch adapted to switch on said at least one UV emitter when the housing is mounted on the container.

4. An apparatus as claimed in claim 1, wherein said receiving means includes a feed hopper, an insert having two sides defining a feed slot therebetween, feed rolls arranged in the feed slot, and a plurality of transport shafts having guides thereon which convey the scrap material into said chopper, and wherein the feed rolls, the transport shafts, and the chopper are disposed in the insert and the insert is made from a material selected from the group consisting of UV-transparent glass and UV-transparent plastic.

5. An apparatus as claimed in claim 4, wherein a UV emitter is arranged in a curved UV reflector on each of said two sides and outside of said insert and wherein the apparatus further comprises means for providing an air-feed of cooling air to said at least one UV emitter.

6. An apparatus as claimed in claim 4, wherein one of the feed rolls and the chopper are jointly connected via a continuous loop sprocket chain which is passed over sprocket wheels on an axle of the feed roll and a shaft of the chopper, and wherein the apparatus contains a motor capable of setting a first chopping shaft of the chopper in motion via a further sprocket chain, on which the first chopping shaft is mounted a sprocket wheel which meshes with a sprocket wheel on a second chopping shaft of the chopper and wherein this sprocket wheel engages with a sprocket wheel on the shaft of the chopper.

7. An apparatus as claimed in claim 4, further comprising a photocell arranged in said feed slot, and a motor, wherein the photocell controls the switching on and switching off of the motor in accordance with the entry and throughflow of said photopolymerizable scrap material.

8. An apparatus as claimed in claim 1, wherein said chopper is arranged downstream of said at least one UV emitter.

9. The apparatus as claimed in claim 1, wherein said chopper is provided upstream of said at least one UV emitter.

10. The apparatus as claimed in claim 9, wherein said housing includes a feed slot below which said chopper is arranged, said chopper is provided with a chopping shaft directly driven by a motor, and wherein said apparatus further comprises a cylindrical insert made of a material selected from the group consisting of UV-transparent glass and UV-transparent plastic which is open at top and disposed beneath said chopper, said housing further being provided with a flap door which when opened allows said insert to be removed, and wherein said at least one UV emitter is rod-shaped and mounted vertically on an inner surface of said housing which faces said UV-transparent cylinder.

11. An apparatus as claimed in claim 1, further comprising an endless conveyor belt, horizontally running over two end rollers, and arranged in said housing, wherein said receiving means includes a feed hopper which extends into the interior of the housing and ends above the conveyor belt, said at least one UV emitter is mounted above the conveyor belt downstream of said feed hopper, and the chopper is provided laterally displaced to, and below, an end roller which is downstream of said UV emitter.

12. An apparatus as claimed in claim 11, wherein the feed hopper is curved in the housing interior in the direction of motion of a top strand of the conveyor belt.

13. The apparatus as claimed in claim 11, wherein a guide element lies on the conveyor belt in the region of one of the end rollers, and the guide element discharges the scrap material into the chopper, and below the chopper is arranged a scrap container.

* * * * *